Figure 1:
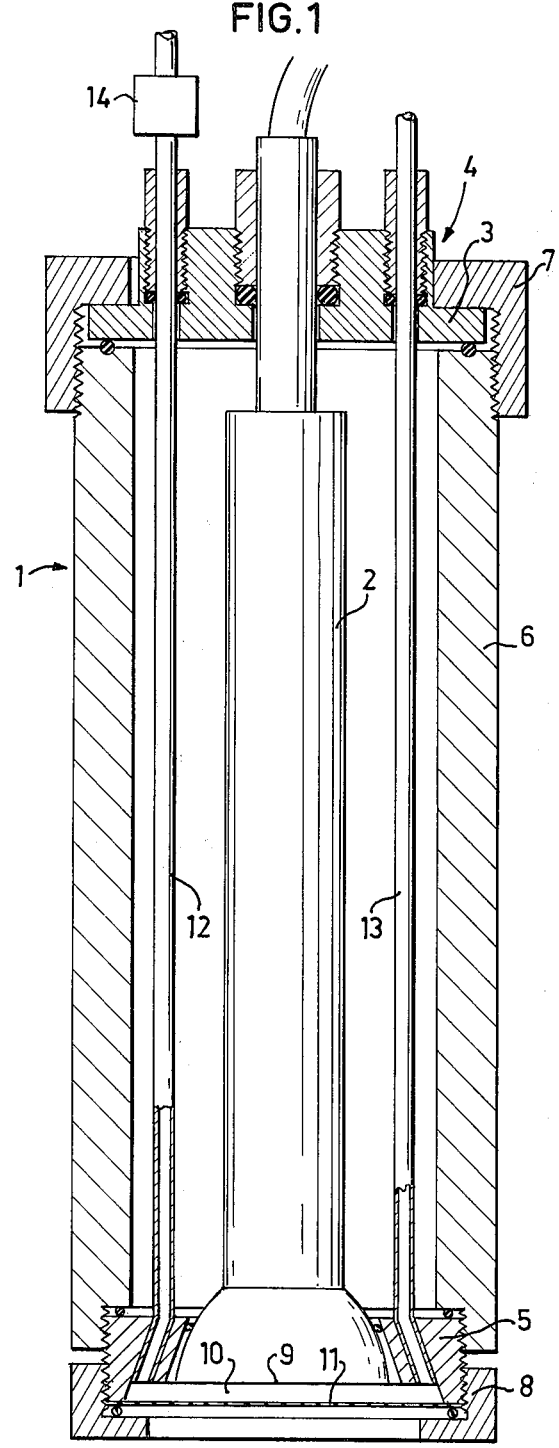

United States Patent [19]

Enfors et al.

[11] 4,024,042
[45] May 17, 1977

[54] ENZYME ELECTRODE

[75] Inventors: Sven Olof Enfors; Nils Ludvig Molin, both of Lund; Klaus Hermann Mosbach, Furulunds Station; Hans Jörgen Nilsson, Lund, all of Sweden

[73] Assignee: Servo Chem AB, Vallingby, Sweden

[22] Filed: Mar. 17, 1976

[21] Appl. No.: 667,864

[30] Foreign Application Priority Data

Mar. 27, 1975 Sweden .............................. 7503652

[52] U.S. Cl. .......................... 204/195 P; 204/1 T; 204/195 B; 195/103.5 R; 195/122
[51] Int. Cl.² ..................... G01N 27/46; C12K 1/04
[58] Field of Search ............ 204/1 E, 195 P, 195 B; 195/103.5 R, 103.5 C, 121, 122

[56] References Cited

UNITED STATES PATENTS

| | | | |
|---|---|---|---|
| 3,239,430 | 3/1966 | Aiba et al. | 195/122 |
| 3,467,590 | 9/1969 | Gibson et al. | 204/195 L |
| 3,494,723 | 2/1970 | Gray | 195/121 |
| 3,539,455 | 11/1970 | Clark | 204/1 E |
| 3,770,607 | 11/1973 | Williams | 204/195 B |
| 3,838,011 | 9/1974 | Hagen et al. | 195/103.5 R |
| 3,838,033 | 9/1974 | Mindt et al. | 204/195 B |
| 3,838,034 | 9/1974 | Groves | 204/195 B |
| 3,902,970 | 9/1975 | Levin | 195/103.5 C |
| 3,948,745 | 4/1976 | Guilbault et al. | 204/195 P |

*Primary Examiner*—T. Tung
*Attorney, Agent, or Firm*—Young & Thompson

[57] ABSTRACT

The invention relates to an enzyme electrode which can be sterilized and regenerated and which has a sensitive surface and an enzyme in contact therewith. A semipermeable membrane is arranged at a distance from the sensitive surface of the detecting electrode and defines a chamber containing the enzyme which is supplied to and discharged from the chamber through a supply conduit and a discharge conduit, respectively. A sterilization device for the enzyme is arranged in the supply conduit for the enzyme. The enzyme electrode is produced by means of the detecting electrode being sterilized in a manner known per se and by means of the enzyme being led into a chamber via a sterilization device through a supply conduit for contact with the sensitive surface of the detecting electrode and for contact with the semipermeable membrane arranged at a distance from said sensitive surface. The enzyme is continuously or intermittently supplied through the supply conduit simultaneously as previously supplied enzyme is discharged from the chamber through the discharge conduit.

5 Claims, 2 Drawing Figures

ENZYME ELECTRODE

The present invention relates to an enzyme electrode which can be sterilized and regenerated and which comprises a detecting electrode and an enzyme in direct or indirect contact therewith. Said enzyme electrode has the characteristics disclosed in claim 1.

The invention also relates to a process for the production of the enzyme electrode according to the above. Said process has the characteristics disclosed in claim 7.

The enzyme electrode is intended to be used in qualitative and quantitative analysis of substances, for example in connection with fermentation processes or within the medical area for in vivo measurements of metabolites (e.g. glucose, urea etc.). The enzyme electrode is therewith exposed to the medium which is to be analysed with respect to the substrate of the enzyme. If the substrate of the enzyme exists in the solution, said substrate is conveyed via a semi-permeable film or membrane applied onto the enzyme electrode to an enzyme layer between the membrane and the detecting electrode, whereby an enzyme reaction is obtained, said enzyme reaction being registered by the detecting electrode. Alternatively, the consumption of substrate in the enzyme layer can be registered. The signal which is detected by the detecting electrode is a measure of the substrate concentration.

In a previously known construction of the enzyme electrode, a carrier, for example a nylon web, to which an enzyme is applied in the gel phase is brought into close contact with the electrode, after which a semi-permeable membrane is drawn over said carrier.

In another previously known embodiment the enzyme is enclosed by means of a semi-permeable membrane in a thin liquid layer around the sensitive surface of (the detecting) electrode.

The use of these previously known enzyme electrodes in fermentation processes has above all been restricted by difficulties in sterilizing the electrode and the limitations of the term of life of the enzyme, this latter factor mainly due to the inactivation of the enzyme during continuous operation in complex media.

The simplest and most effective method of sterilizing the detecting electrode is sterilization in an autoclave. However, the enzyme cannot be sterilized in an autoclave and, thus, the enzyme must be sterilized separately in another manner and thereafter mechanically applied onto the detecting electrode. However, the demand for sterility is great and even a short term exposure to air entails unsterility and, thus, this demand is very hard to meet in previously known enzyme electrodes. Furthermore, it is difficult to regenerate such enzyme electrodes during operation.

In the use of enzyme electrodes in a fermentation process, the activity of the enzyme decreases with time, often so rapidly that the electrode cannot be put to practical use.

The purpose of the present invention is to obtain an enzyme electrode whose essential parts can be sterilized in an autoclave.

A further purpose of the present invention is to obtain an enzyme electrode which can be used in continuous measurements for a longer period of time than has hitherto been possible.

The enzyme electrode according to the present invention comprises a detecting electrode and an enzyme which is directly or indirectly in contact with the same, a semi-permeable membrane being arranged at a distance from the sensitive surface of the detecting electrode and defining a chamber containing the enzyme. A supply conduit and a discharge conduit are arranged for the supply and discharge of the enzyme. The supply conduit can be provided with a sterilization device for the enzyme. The enzyme is usually present as a solution, but can also comprise a suspension of immobilized enzymes. The enzyme can be covalently bond to a bearer, absorbed to a bearer contained in a cross-linked bearer, microencapsulated or cross-linked enzyme aggregate. Immobilization of enzymes often leads to greater stability (longer term of life). Enzymatic reactions calling for coenzymes can also be used by means of the coenzyme, commonly nicotinamidadenine dinucleotides NAD (H) and NADP (H), being bound to water-soluble bearers such as dextrane and being supplied through the supply conduit in an analogous manner.

In a preferred embodiment of the present invention the sterilization device is a membrane filter, but a radiation sterilizer or some other suitable sterilization device can also be used.

The electrode can first be sterilized without the enzyme in an autoclave, after which the enzyme is supplied through the supply conduit and allowed to pass through the sterilization device and into the enzyme chamber of the electrode. This is possible to construct as all of the details included in the electrode can be treated in an autoclave.

Preferably the enzymes exist in the form of a solution. The enzyme can advantageously be used in the form of a suspension of microencapsulated enzymes.

Furthermore the enzyme in the electrode can be continuously or intermittently replaced in and for regeneration of the enzyme electrode. In this manner the electrode can be used for continuous measurements during long periods of time.

Figure 2:
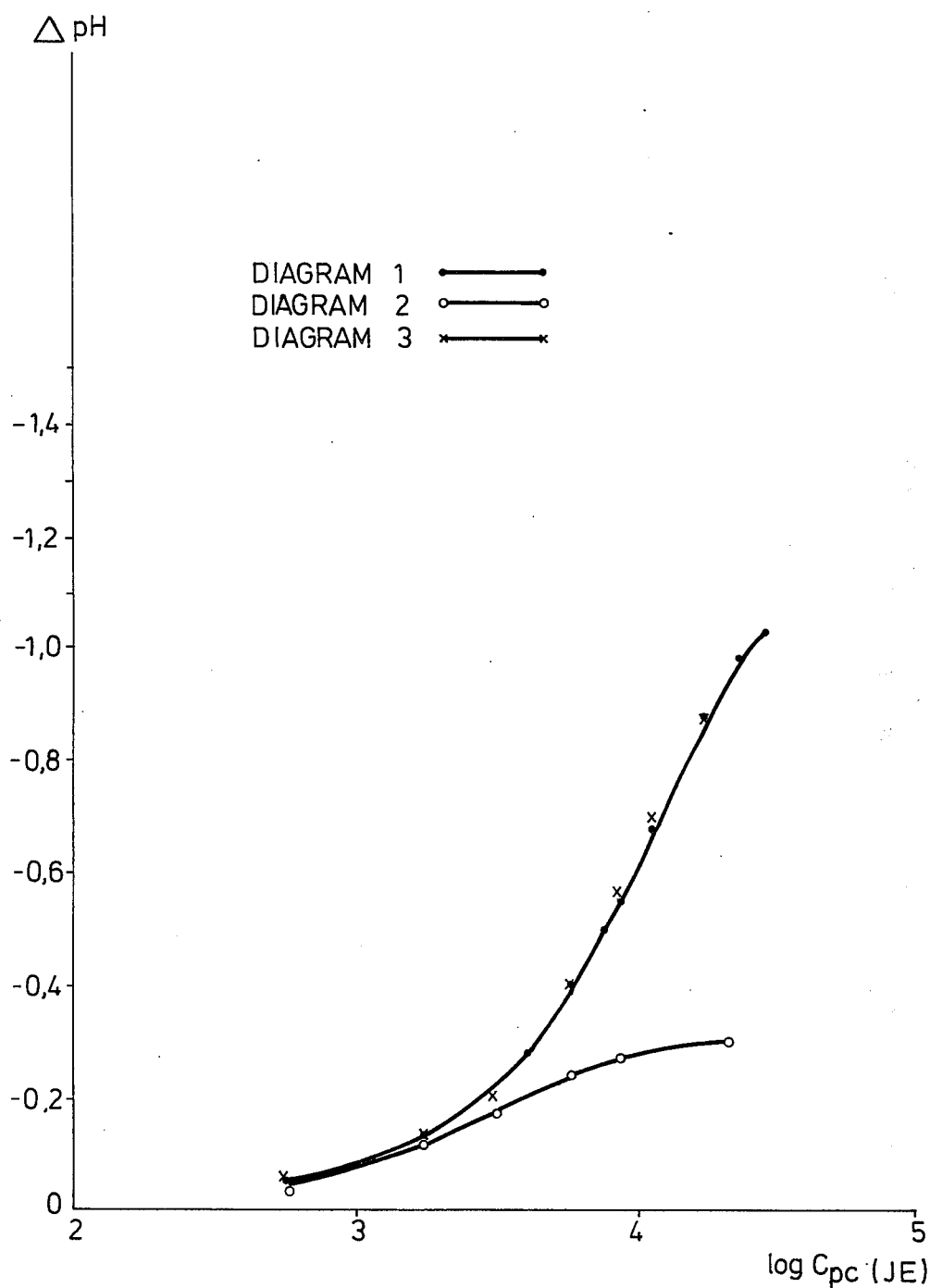

In the enclosed drawings FIG. 1 shows a preferred embodiment of the present invention while FIG. 2 is a diagram of a regeneration of the enzyme electrode according to the present invention.

In FIG. 1 reference numeral 1 denotes an enzyme electrode according to the present invention. This enzyme electrode 1 consists of a pH electrode 2 mounted in a holder which, in its entirely, has been denoted with 3. The holder 3, which is cylindrical, consists of an upper lead-in 4 for the electrode 2 and a lower lead-in 5, both of which lead-ins are held together by a spacing collar 6 by means of two screw seals 7 and 8. Two O-rings seal the container. The pH electrode 2 is mounted in the middle of the container 3 so that its sensitive surface 9 is situated in the lower plane of the lower lead-in 5. A semi-permeable membrane 11 is, by means of the screw seal 8, mounted directly under the sensitive surface of the pH electrode and defines a chamber 10 for the enzyme solution. A supply conduit 12 and a discharge conduit 13 are inserted through the upper and lower lead-ins 4 and 5 and open into the chamber 11. The supply conduit 12 comprises a sterilization device 14 in the form of a membrane filter.

When preparing the enzyme electrode, the entire enzyme electrode 1 is first sterilized without the enzyme, after which the enzyme solution is led through the supply conduit 12 via the sterilization device 14. The enzyme electrode is thereafter prepared for use. New enzyme solution can be continuously or intermittently supplied via the supply conduit 12, whereby it is simultaneously sterlized. The original enzyme solution is therewith forced out of the chamber via the discharge conduit 13.

Naturally the selection of the detecting electrode and the enzyme preparation depends on the kind of reaction which is to be controlled by the enzyme electrode. Examples of electrodes other than the pH electrode are an oxygen electrode and an $NH_4^+$ electrode.

FIG. 2 reveals a diagram of a regeneration of the above-described enzyme electrode. As an example, the measuring of the penicillin concentration in a fermentor has been chosen in which the detecting electrode is a pH electrode and the enzyme is a solution of penicillinase. Curve 1 (dots) discloses a calibration curve for the enzyme electrode prior to use. Curve 2 (circles) discloses the response of the enzyme electrode after 50 hours' use (after which the electrode is totally unusable). Finally curve 3 (crosses) discloses the response of the electrode after regeneration in accordance with the above-described regeneration process. The diagram reveals that full reproducability can be obtained during regeneration.

The above-described embodiment of the present invention has been described for purposes of illumination and is not intended to restrict the invention to said embodiment.

What we claim is:

1. An enzyme electrode which can be sterilized and regenerated, comprising a detecting electrode having a sensitive surface and an enzyme in direct or indirect contact with the same, characterized in that a semipermeable membrane is arranged at a distance from the sensitive surface of the detecting electrode and defines a chamber containing the enzyme and that a supply conduit and a discharge conduit are arranged for the supply and discharge of the enzyme, said supply conduit including a sterilization device for the enzyme.

2. Enzyme electrode according to claim 1, characterized in that the enzyme is present in the form of a solution.

3. Enzyme electrode according to claim 1, characterized in that the enzyme is present in the form of a suspension of immobilized enzymes.

4. Enzyme electrode according to claim 1, characterized in that the sterilization device is a membrane filter.

5. Enzyme electrode according to claim 1 characterized in that the sterilization device is a radiation sterilizer.

* * * * *